United States Patent [19]

Pavlik et al.

[11] B 4,015,612

[45] Apr. 5, 1977

[54] FILM-FORMING POLYMER MODIFIED WITH A FLUOROALIPHATIC RADICAL CONTAINING COMPOUND AND HAIR STYLING COMPOSITION THEREOF

[75] Inventors: Frank J. Pavlik, St. Paul; Robert L. Hansen, Roseville, both of Minn.

[73] Assignee: Minnesota Mining and Manufacturing Company, St. Paul, Minn.

[22] Filed: Apr. 26, 1974

[21] Appl. No.: 464,491

[44] Published under the second Trial Voluntary Protest Program on March 30, 1976 as document No. B 464,491.

Related U.S. Application Data

[63] Continuation of Ser. No. 758,630, Sept. 9, 1968, abandoned.

[52] U.S. Cl. .................................. 132/7; 8/127.51; 424/DIG. 1; 424/DIG. 2; 424/47; 424/71; 526/14; 526/46; 526/248; 526/249; 526/271

[51] Int. Cl.² ...................... A45D 7/00; A61K 7/11

[58] Field of Search ............ 8/127.51; 424/DIG. 1, 424/DIG. 2, 70, 71; 260/80.8, 78.5 BB, 78.5 T; 132/7

[56] References Cited

UNITED STATES PATENTS

| | | | |
|---|---|---|---|
| 3,026,250 | 3/1962 | Coyner | 424/71 X |
| 3,137,713 | 6/1964 | Shen et al. | 424/71 X |
| 3,245,817 | 4/1966 | Lovness | 260/556 F X |
| 3,384,627 | 5/1968 | Anello et al. | 260/80.8 X |

Primary Examiner—V. D. Turner
Assistant Examiner—Vera C. Clarke
Attorney, Agent, or Firm—Alexander, Sell, Steldt & DeLaHunt

[57] ABSTRACT

Hair styling compositions which have excellent holding characteristics at elevated humidity and impart a soft hand and natural sheen to hair comprising a solution of a film-forming polymer modified with a fluoroaliphatic radical containing compound are disclosed.

7 Claims, No Drawings

FILM-FORMING POLYMER MODIFIED WITH A FLUOROALIPHATIC RADICAL CONTAINING COMPOUND AND HAIR STYLING COMPOSITION THEREOF

This is a continuation of application Ser. No. 758,630, filed Sept. 9, 1968, now abandoned.

The present invention relates to the art of hair styling and more particularly to hair styling compositions which are typically applied to styled hair in a spray, liquid or gel form.

The art of hairdressing has undergone a transition from the chemical "permanent waving" process involving strong chemicals, offensive odors, and time-consuming procedures to the relatively simple technique of styling hair involving combing of the hair into the desired configuration and depositing upon the so configured hair a thin coating of a hair styling composition comprising a polymer film to retain the coiffure despite wind, weather, and mechanical agitation.

At first glance, the requirements for such a hair styling composition appear simple and indeed, the early preparations consisted of nothing more than alcohol solutions of shellac. However, in actual commercial practice, a relatively sophisticated set of properties must be combined to meet the requirements of performance and esthetic appeal. Primarily, of course, the polymer film must hold the hair in place despite high humidity, wind, and the rigors of the modern dance. On the other hand, the hair must not feel stiff or harsh nor become brittle. The film should not flake off creating artificial dandruff. The film should not become soft, sticky or tacky in high humidity, yet it must be sufficiently water soluble to be readily removed by shampoos. The deposited resin should be transparent, colorless, form a continuous film, and provide the glossy sheen of natural, healthy hair. The hair styling composition should be compatible with a variety of other hairsprays so that it can be readily used for touchup of a previously arranged hairdo. In order to be conveniently formulated, the resin should be soluble in ethyl alcohol and in a combination of ethanol with either a hydrocarbon or a halohydrocarbon propellant, such as is used in ordinary household or industrial spray dispensers.

The resins may also be applied in the form of a spray, gel, foam, or latex solution to hair shaped on, for example, rollers. The treated hair is generally allowed to dry before being combed out, providing a resilient wavy hair style.

A number of polymer systems are found in hair styling compositions. One such system is based on polyvinyl pyrollidone, a polar non-ionic water soluble material which, when dry, is quite soft and flexible, but at even moderate humidities becomes soft and readily loses its holding power. A second system attempts to improve the water resistance of the polymer by copolymerizing vinyl pyrrolidone with vinyl acetate, but even this material is still quite water sensitive. A commonly used polymer system is based on the alternating copolymer of maleic anhydride and a vinyl alkyl ether, usually vinyl methyl ether. This polymer itself is somewhat too rigid to have the proper physical characteristics, being somewhat harsh, so it is usually modified by the use of external plasticizers and by reaction with, for example, long chain aliphatic alcohols. Reaction with the modifying alcohols or with the ethanol normally present in the formulation results in a high incidence of free carboxyl groups, providing a polar ionic character. While this latter system provides the best balance of properties presently available, it is somewhat too harsh and stiff even when modified; even when sufficient plasticizer is added to reduce the harshness of the polymer, holding power, particularly in relatively high humidities, is considerably reduced.

It has now been found that modification of a film-forming resin for use in hair treating compositions with materials containing a fluoroaliphatic radical provides a resin with a superior balance of properties between the requirements of softness and curl retention, and surprisingly gives markedly improved holding characteristics at elevated humidity.

In the preparation of the modified film-forming polymer, the fluoroaliphatic radical may be incorporated either in the form of a comonomer during the polymerization of the film-forming polymer, or it may be attached by subsequent chemical reaction to a preformed polymer. In the former case, the fluoroaliphatic radical may comprise a portion of an ethylenically unsaturated monomer of suitable relative reactivity. For example, in the maleic anhydride copolymer system the fluoroaliphatic radical could comprise a portion of a vinyl ether.

For subsequent incorporation, the fluoroaliphatic radical containing molecule will also contain one or more suitable functional groups, such as, for example, a primary or secondary amine group, a carboxyl group, a hydroxyl group, an isocyanate group, and the like. In the case of modifying a preformed maleic anhydride-vinyl alkyl ether copolymer, a molecule containing a fluoroaliphatic radical and also a hydroxyl group is particularly convenient. The particular functional group is, of course, not critical in the final performance of the polymer although it may influence to some extent the characteristics of the final film; however, the group selected should be one which is conveniently available and which reacts readily with the particular polymer selected for modification, as is well understood in the art.

The fluoroaliphatic radical, $R_f$, can be generally described as a fluorinated saturated monovalent non-aromatic radical. The aliphatic chain may be straight, branched or, if sufficiently large, cyclic and may include oxygen atoms or trivalent nitrogen atoms bonded only to carbon atoms. A fully fluorinated radical is preferred, but hydrogen or chlorine atoms may be present as substituents, provided that not more than one atom of either is present for every two carbon atoms and preferably, the radical contains at least a terminal perfluoromethyl group. It is not clear why the fluoroaliphatic radical confers the desirable properties on the polymer since, in many cases, the resulting film is not strongly oleophobic or hydrophobic by the standard tests. It may have to do with imparting a resistance to transfer of moisture through the film to the hair. In any event, it has been found that fluoroaliphatic radicals containing at least three fluorinated carbon atoms are useful and that radicals containing up to twenty fluorinated carbon atoms can perform satisfactorily. In general, longer chains are more difficult and expensive to obtain and provide less efficient utilization of fluorine than those containing less than about twenty carbon atoms. A preferred chain length is about five to about twelve carbon atoms.

An exemplary structure for the fluoroaliphatic radical containing molecule would be:

$R_fQ_pZ$, wherein $R_f$ is a fluoroaliphatic radical as described above, Q is a multivalent, generally divalent linking group, including one or more groups such as alkylene, ($-C_nH_{2n}-$), wherein n is an integer from one to about 15; oxyalkylene $(C_qH_{2q}O)_m$, wherein q is an integer from two to about four and m is an integer from one to about 25; arylene (sucn as phenylene); sulphonamido alkylene (such as $-SO_2NR(C_nH_{2n})$, wherein R is a hydrogen atom or a lower alkyl group of one to about four carbon atoms, and n is an integer from about one to 15; carbonamido alkylene (such as $CONR(C_nH_{2n})$, wherein R is hydrogen or a lower alkyl group and n is an integer from about one to fifteen, and the like and p is 0 or 1. It will be noted that in some instances more than one $R_f$ group may attach to a single Q group, and in other instances a single $R_f$ group may be linked to more than one Q group, or may be linked by a single Q group to more than one Z group and in some cases Q may not be present at all, as in compounds such as $R_fCO_2H$. The Z group represents a functional group capable of chemically bonding the $R_f$ group to the film-forming polymer. Typical Z groups would include NCO; $-CO_2M$, where M is a metal, $NH_4$ or H radical; -NRH, wherein R represents a hydrogen atom or a lower alkyl group of one to four carbon atoms; $-SR'$; and $OR'$ wherein R' equals $-H$ or $-CH=CH_2$. Exemplary $R_fQZ$ compounds would include:

$C_8F_{17}SO_2N(C_2H_5)CH_2CH_2OH$ $C_8F_{17}SO_2N(C_2H_5)CH_2CH_2NH_2$ $C_8F_{17}SO_2N(CH_3)CH_2CHOHCH_2OH$ $C_7F_{15}CON(CH_3)CH_2CH_2OH$ $C_4F_9SO_2NHCH_2CH_2OH$

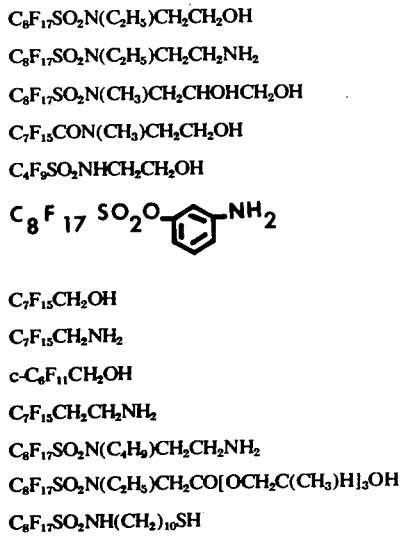

$C_7F_{15}CH_2OH$ $C_7F_{15}CH_2NH_2$ $c-C_6F_{11}CH_2OH$ $C_7F_{15}CH_2CH_2NH_2$ $C_8F_{17}SO_2N(C_4H_9)CH_2CH_2NH_2$ $C_8F_{17}SO_2N(C_2H_5)CH_2CO[OCH_2C(CH_3)H]_3OH$ $C_8F_{17}SO_2NH(CH_2)_{10}SH$ $C_8F_{17}SO_2N(CH_3)CH_2CH_2NCO$ $C_8F_{17}SO_2N(CH_3)CH_2CH_2OCH=CH_2$ $CF_3CF_2CF_2OC(CF_3)FCH_2OH$ $CF_3CF_2CF_2O[CF(CF_3)CF_2O]_3C(CF_3)FCH_2OH$ $CF_3O(CF_2O)_4CF_2CO_2H$ $C_{20}F_{41}CH_2CH_2OH$

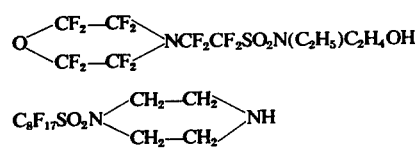

$C_8F_{17}SO_2N(C_2H_5)CH_2CONHCH_2CH_2NH_2$ $C_8F_{17}SO_2N(C_2H_5)CH_2CH_2O_2CNHC_6H_3CH_3NCO$

The fluorine content (the fluorine being present in the form of fluoroaliphatic radicals) of the modified film-forming polymer controls the characteristics of the hair treating composition. While as little as 0.5 percent by weight of fluorine in the form of $R_f$ groups produce a noticeable improvement over comparable unmodified material, at least 1% is generally required for satisfactory performance. Beyond about 15 percent by weight of fluorine, little appreciable additional advantage is obtained. If the fluorine content exceeds about 25 percent by weight, the modified polymer becomes only difficultly soluble in ethanol with a resultant decrease in utility.

Film-forming polymers suitable for modification should be linear (i.e., not crosslinked), and of sufficiently high molecular weight to maintain the hair in the desired shape. When such polymers are dissolved in a volatile solvent to form a dilute solution, the solution poured onto a substrate, and the solvent allowed to evaporate, a more or less continuous film of polymer is left coating the substrate. If the molecular weight is too high, the viscosity of solutions is too great and application becomes difficult. In general, a solution containing one percent by weight of the polymer in a suitable aprotic solvent will exhibit a specific viscosity at 25°C. of at least about 0.05 and no greater than about 4, preferably about 0.1 to 2. Suitable solvents include hydrocarbons, halogenated hydrocarbons, aliphatic ketones, and the like, the only requirement being that the polymer be soluble to at least about 5 percent by weight at room temperature. Methyl ethyl ketone is a particularly useful solvent.

The polymer, in order to be modified, must contain a multiplicity of pendant (i.e., linked to the skeletal chain) functional groups capable of undergoing reaction with the modifying fluoroaliphatic containing reactant to form a stable compound. Exemplary suitable pendant groups include hydroxyl, carboxyl, primary or secondary amino, isocyanate, and the like. Carboxyl groups are particularly desired since residual unreacted carboxyl groups do not unduly increase the sensitivity of the film to moisture, while improving solubility and hence ease of removal in the mildly basic shampoo solution commonly used to clean the hair.

Suitable carboxyl-containing polar polymers include copolymers of maleic anhydride, fumaric acid, acrylic acid and the like with ethylene, alkyl vinyl ethers such as methyl vinyl ether, acrylic esters such as ethyl acrylate, vinyl pyrollidone and the like. A useful carboxyl-containing polar polymer may contain no carboxyl groups as such, but will then contain, for example, anhydride or ester groups which are subsequently converted by chemical reaction to free carboxyl groups.

An exemplary carboxyl containing polar polymer is the alternating copolymer of maleic anhydride and methyl vinyl ether, which contains repeating units of the structure:

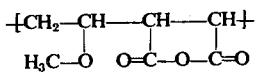

Reaction with a modifying fluoroaliphatic radical containing compound can be exemplified by:

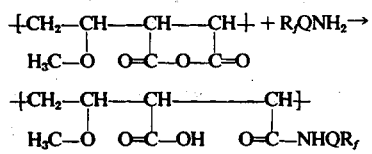

In the case of amide derivatives, it is frequently desirable to react the product with a low molecular weight anhydride such as acetic anhydride to form the cyclic imide:

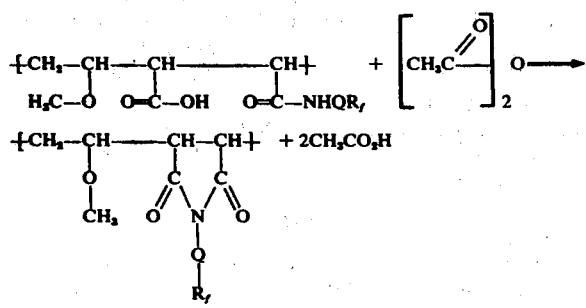

The resulting modified polymer then comprises a skeletal chain having appended therefrom fluoroaliphatic radicals linked through the Q group to the chain by one or more multivalent, generally divalent, linking radicals such as ester, thioester, ether, amide and imide.

As little as 0.1 percent of the anhydride groups in the polymer may be reacted with the fluoroaliphatic radical containing compound or, substantially all of the anhydride groups can be reacted depending on the level of fluoroaliphatic modification desired for the final product. Generally, sufficient of the compound is added to react with from about 0.25 to 50 percent of the anhydride units, shorter fluoroaliphatic radicals usually requiring larger percent conversion to achieve a given level of modification. Usually modification of the resin does not significantly alter the specific viscosity of the polymer.

In preparing a hair styling composition, the modified polymer is customarily dissolved in alcohol or an aqueous alcohol solution, and the remaining unreacted anhydride groups are converted to ester and acid groups:

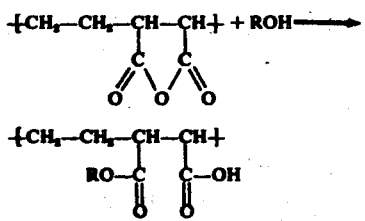

In order to avoid undue moisture sensitivity and still provide adequate solubility in mildly alkaline solution for ease of removal during washing, the carboxyl group containing modified polymer, after solution in alcohol, should comprise between about five and 22 percent by weight of free carboxyl groups, preferably between about 10 to about 22 weight percent.

One general method of predicting the suitability of a modified polymer for the purposes of the present invention involves the determination of the hardness of the film formed. This is accomplished by applying a solution of the polymer to a glass plate, evaporating the solvent, and determining the hardness of the resulting film (which should be between about 10 and 100 mils thick). The test film can be conveniently prepared from an aerosol formulation by spraying onto a plate, allowing the plate to dry at room temperature for 15 minutes to 1 hour and determining the hardness by means of the Sward Rocker Hardness test. This test is described in the text authored by D. H. Parker, *Principles of Surface Coating Technology*, published in 1965 by Interscience Publishers, New York, particularly on page 486. Generally speaking, a Sward hardness of about 40 to 65 is preferred. Materials having a hardness below about 35 generally are too soft and lack holding power, while materials having a hardness above about 75 feel too harsh, making combing difficult and providing an unnaturally stiff feeling to the hairdo. As will be pointed out hereafter, many polymers modified with conventional hydrocarbon derivatives have hardness values within the specified desirable range, but still fail to give a satisfactory balance or properties, while a film formed from compositions modified by fluoroaliphatic radicals as above described, generally performs satisfactorily and has the proper esthetic characteristics as well as possessing the necessary physical and chemical characteristics to allow commercial utilization in essentially standard formulations.

The following Examples illustrate typical methods of preparing fluoroaliphatic modified resins of the present invention.

EXAMPLE I

To 1200 g. of methyl ethyl ketone (solvent) was added 156 g. of a low molecular weight alternating copolymer of methyl vinyl ether - maleic anhydride having a specific viscosity (1% solution in methyl ethyl ketone) at 25°C. of about 0.2 to 0.5 (Gantrez AN119), and then 138 g. of N-ethyl perfluorooctanesulfonamidoethyl alcohol. The solution was heated and stirred 27 hrs. at about 80°C.; then 50 g. of anhydrous ethyl alcohol was added and heating and stirring was continued for 18 hrs. The solution was evaporated to dryness to remove the methyl ethyl ketone. Purification was accomplished by precipitating the resin in heptane and twice extracting the resin with additional hot heptane. A resin product containing 7.2% fluorine was obtained, which, when formulated into a hair treating composition, exhibited good curl retention and other desirable properties of a hair spray.

EXAMPLE II (a) To 346 g. of β(N-ethyl perfluorooctanesulfonamide) ethyl alcohol dissolved in 1300 g. of methyl ethyl ketone was slowly added 390 g. of methyl vinyl ether-maleic anhydride copolymer (Gantrex AN119), additions being to the vortex of the rapidly stirred solution at 50°C. The mixture was heated at reflux for 24 hrs. 101 g. anhydrous ethyl alcohol was added and heating at reflux continued for 16 hrs. The solution was then poured into 1800 ml. heptane with stirring. The coagulated polymer was separated, mechanically broken up and twice extracted with 1800 ml. portions of hot heptane. The resin was then dried in vacuo at 60°C./20 mm. overnight. 540 g. of the resin (Resin (a)) was recovered.

In a similar manner, other fluoroaliphatic radical-containing alcohols were each reacted with the methyl-vinyl ether-maleic anhydride copolymer in the ratio of 0.25 mol alcohol per anhydride equivalent of the copolymer to form hair treating resins:

EXAMPLE III 6.9 grams (0.0125 m.) of β(N-ethylperfluorooctanesulfonamide) ethanol and 40 g. methyl isobutyl ketone were stirred and heated to solution. 6.3 g. (0.05 anhydride equivalents) of ethylene-maleic anhydride copolymer (EMA11, Monsanto) was added and heating and stirring continued for 23 hrs. Absolute ethanol, 3.0 g., was added to react with unreacted anhydride groups. The reaction mixture was heated for 16 additional hrs., then cooled and added to 75 ml. of heptane. The coagulated polymer was collected, washed and extracted twice with additional 75 ml. portions of hot heptane, then dried in vacuo at 60°C./20 mm Hg.

EXAMPLE IV 3.0 g. of 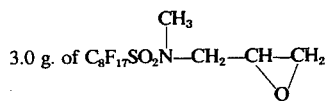

and 12 g. of orange flake shellac were heated to reflux temperature in 100 g. of methyl ethyl ketone, to which 0.5 g. of $(C_2H_5)_3N$ was added and stirring and heating continued for 8 hrs. The flask contents were then poured into a petri dish and the solvent evaporated. The residual resin was extracted two times with 50 ml. of isopropyl ether and dried in vacuo overnight at 60°C./20 mm. The dried resin readily dissolved in ethanol.

EXAMPLE V

A solution of 5.7 g. of a commercial copolymer of maleic anhydride and methyl vinyl ether (Gantrez AN119) was dissolved in 25 ml. of methyl ethyl ketone at about 75°C. To this was added dropwise, with rapid stirring, a solution of 1.0 g. of the amine $C_8F_{17}SO_2N(C_2H_5)CH_2CH_2NH_2$ in 3 ml. of methyl ethyl ketone. The solution was maintained at 50°C. for 10 minutes, then 1.5 ml. of acetic anhydride was added to effect imidization of the amic acid initially formed. This solution was kept at 75°C. for 30 minutes, then poured into a tray and warmed to 80°C. overnight in a circulating air oven. The resulting clear, hard, solvent free film was ground to a fine powder.

Samples of these modified resins were dissolved in absolute alcohol with heating and shaking. The resulting approximately 2% solutions were clarified by filtration, then tested for curl retention.

Alcohol-resin solutions were compounded in the following proportions by weight and subsequently tested as a hair treating composition. Hair treated with these alcohol-resin solutions exhibited excellent oil repellency and resistance to dry soil.

| Composition | $C_8F_{17}SO_2N(C_2H_5)CH_2CH_2NH_2$ | Resin |
|---|---|---|
| (a) | 1% | 99% |
| (b) | 5% | 95% |
| (c) | 10% | 90% |
| (d) | 15% | 85% |
| (e) | 25% | 75% |
| (f) | 50% | 50% |

A modified resin was prepared by substituting butyl amine, $n-C_5H_{11}NH_2$, for the fluoroaliphatic amine in the same mole percentages as in Example V(d). Hair treated with this fluorine-free modified resin showed comparable curl retention to the Example V(d) fluoroaliphatic modified resin but felt quite harsh, and, of course, had no oil repellency or dry soil resistance properties.

EXAMPLE VI 2.3 g. (0.004 moles) of $C_8F_{17}SO_2N(CH_3)CH_2CH_2OCH=CH_2$, 3.1 g. (0.03 moles) of maleic anhydride, 0.036 g. of benzoyl peroxide and 7.09 g. of methyl ethyl ketone were charged to a 1 × 7 inch glass ampoule. After evacuating, purging with nitrogen and cooling, 1.6 g. (0.028 moles) of methyl vinyl ether (at −10°C.) was added. The sealed ampoule was tumbled in a water bath at 50°C. for 16 hours. A clear very viscous polymer solution was obtained which was diluted with methyl ethyl ketone to 17.4 percent solids. Conversion after warm heptane and benzene washes was 99.4 percent. The polymer (Resin (a)) was precipitated by pouring the solution into a large volume, about 150 ml., of heptane (60°C.) with agitation. The polymer was filtered off and dried at room temperature.

2.0 g. of the dried polymer and 98.0 g. of ethyl alcohol were charged to a 200 ml. flask. The mixture was refluxed with stirring for five hours. After approximately 3 hours the polymer was completely in solution. The clear slightly pink solution was submitted for curl retention tests.

Similar terpolymers with the following ratios (by weight) were prepared:

| | $C_8F_{17}SO_2N(CH_3)CH_2CH_2OCH=CH_2$ Parts | Methyl vinyl ether Parts | Maleic anhydride Parts |
|---|---|---|---|
| (b) | 5 | 35 | 60 |
| (c) | 50 | 15.5 | 34.5 |
| (d) | 15.2 | 30.6 | 54.2 |
| (e) | 15.2 | 30.6 | 56.9 (5% Excess) |

Benzoyl peroxide (0.5%) was used as initiator. All polymers were prepared at 40% solids. The same polymerization and work up procedures were employed as described above with the exception of using an explosion-proof Waring blender during the precipitation step.

EXAMPLE VII 6.8 g. of the maleic anhydride-methyl vinyl ether copolymer of Example I and 25.4 g. of methyl ethyl ketone were placed in a 250 ml. two neck flask equipped with a condenser, magnetic stirrer, heating mantle, and nitrogen in- and outlet. The mixture was heated to reflux and stirred for 10 minutes at reflux until a clear solution was obtained. The solution was cooled to room temperature. 1.2 grams of $C_8F_{17}SO_2OC_6H_4NH_2(m)$, prepared in accordance with the method of U.S. Pat. No. 3,346,612, was dissolved in 10.8 g. of methyl ethyl ketone. The amine solution was added slowly to the flask, with continuous vigorous stirring. Reflux was continued for one hour under nitrogen. A clear yellow-brown solution was obtained. The solution was poured into a petri dish and placed into an air circulating oven at 70°–72°C. for 16 hours. A brittle slightly opaque material was obtained.

2.0 g. of this polymer was dissolved in 98.0 g. of ethanol in a 250 ml. one neck flask equipped with magnetic stirrer, heating mantle, and condenser. The solution was refluxed for 5 hours. A clear slightly yellow solution was obtained.

EXAMPLE VIII 4.25 g. of the maleic anhydride-methyl vinyl ether copolymer of Example I and 16 g. methyl ethyl ketone were placed in a 2 oz. screw cap bottle equipped with a magnetic stirrer. The mixture was heated on a steam bath until a clear solution was obtained, and then cooled to room temperature. 0.75 g. of $C_8F_{17}SO_2OC_6H_4NH_2(m)$ dissolved in 6.9 g. of methyl ethyl ketone was slowly added to the bottle with stirring and the capped bottle heated on a steam bath for 1 hour with occasional stirring. 0.375 g. of acetic anhydride was added and heating was continued for an additional ½ hour. The solution was then dried at 100°C. for 16 hours in an air circulating oven, to produce a clear, brittle dried polymer.

2.0 g. of dried polymer and 98.0 g. of ether were placed in a 250 ml. flask equipped with magnetic stirrer and condenser and refluxed for 5 hours. A clear slightly pink solution was obtained.

EXAMPLE IX

| Charge | Grams |
|---|---|
| $C_8F_{17}SO_2N(CH_3)CH_2CH_2O_2CC(CH_3)=CH_2$ | 2.5 |
| Methylmethacrylate | 5.0 |
| Acrylic Acid | 2.5 |
| Azobisisobutyronitrile | 0.075 |
| Tetrahydrofuran | 30 |

The above ingredients were charged to a polymerization bottle. After evacuating and purging the bottle with nirogen, it was sealed and then tumbled in a waterbath at 70°C. for 16 hours. A clear polymer solution was obtained. Conversion based on a warm heptane wash was 91.4 percent.

The curl retention ability of test compositions under conditions of high humidity was determined as follows:

Materials

1. Human hair swatches about 6 inches long, held together at one end with a water insoluble adhesive.
2. Curlers (about 1 inch in diameter) and comb.
3. Paper clips.
4. Humidity chamber (held at 75 percent RH at 80° F.) equipped with a rack and scale graduated in inches.
5. Resin solutions in ethyl alcohol — 2 percent solids.

Procedure

Hair swatch is sprayed with the resin solution to be tested until hair is completely saturated. It is then combed through ten times, rolled firmly on a curler and held in place with a suitable retaining mechanism, then allowed to air dry overnight. The dried curl is gently removed from the curler and by means of a paper clip hung on the rack in the humidity cabinet in such a fashion that the drop in curl due to moisture absorption can be measured in inches. The initial position is noted on the scale and readings are then made at intervals of 1, 24 and 72 hours. Loss of curl in inches is recorded.

Alcohol solutions containing modified resins of the present invention were formulated in the proportions shown in the Examples and tested for curl retention with the results indicated in Table I.

TABLE I

| Modified Resins | Fluorine Content (%) | Sward Hardness | Curl Drop (Inches) 1 hr. | Curl Drop (Inches) 72 hr. |
|---|---|---|---|---|
| Example I | 7.2 | 67 | ¾ | 1.0 |
| Example II(a) | 10.3 | 63 | ¼ | ⅜ |
| Example II(b) | 1.1 | 45 | ¼ | ⅝ |
| Example II(c) | — | 59 | ¼ | ⅜ |
| Example II(d) | — | 36 | ⅜ | ⅞ |
| Example II(e) | — | — | ⅜ | 1.0 |
| Example III | 11.0 | 67 | ⅛ | 1.0 |
| Example V(a) | 0.6 | 80 | 0 | ¾ |
| Example V(b) | — | 72 | ¼ | ½ |
| Example V(c) | 6.5 | 54 | 0 | ¼ |
| Example V(d) | 8.5 | 64 | 0 | ¼ |
| Example V(e) | 14.7 | 70 | ½ | ⅝ |
| Example V(f) | 28.0 | 66 | ⅝ | 1⅛ |
| Example VI(a) | 6.0 | 65 | ⅛ | ⅜ |
| Example VI(b) | 2.2 | 71 | ⅛ | ⅜ |
| Example VI(c) | — | 65 | 1 | 2 |
| Example VI(d) | 6.0 | 59 | ½ | ⅝ |
| Example VI(e) | — | 63 | ¼ | ½ |
| Example VII | 8 | 40 | 0 | ⅛ |
| Example VIII | 8 | 48 | ¼ | ⅝ |
| Example IX | 13.0 | 61 | ⅝ | 1⅛ |

A commercial hair-styling preparation includes, in addition to the liquid medium and the film-forming resin, other auxiliary components such as colorants, perfumes, plasticizers, gelling agents, propellants, corrosion inhibitors and the like. These auxiliary components are not critical to the present invention and are varied, as is well known in the art, by the formulator to suit the particular market for which the preparation is intended.

An illustrative spray preparation is compounded as follows (parts by weight):

| | | |
|---|---|---|
| Modified polymer of Example I | 1 | part |
| Perfume concentrate | 0.1 | part |
| Denatured alcohol | 28.9 | parts |
| $CFCl_3$ | 35 | parts |
| $CF_2Cl_2$ | 35 | parts |

The polymer is dissolved in about 10 parts of alcohol with heating; the solution is cooled to room temperature and the perfume concentrate and remaining alcohol are added. The resulting solution and propellants are then placed in a suitable dispensing container.

For a hair set preparation, illustrative formulations are:

| | | |
|---|---|---|
| Modified polymer of Example I | 4 | parts |
| Denatured alcohol | 37.6 | parts |
| Triethanolamine | 0.4 | part |
| Water | 58 | parts |

The polymer is added to the alcohol at room temperature and the suspension rapidly stirred while the triethanolamine, dissolved in the water, is added. Stirring is continued until a clear solution results.

In place of the triethanolamine an equivalent amount of another water-soluble amine such as morpholine, ammonia, ethanolamine and the like may be used to assist in dissolving the resin.

In general, only sufficient amine is added to form a clear solution in the water-alcohol medium, higher water: alcohol ratios requiring somewhat higher quantities of amine. Amine in quantities greater than about 12 percent by weight on the basis of polymer weight tends to produce an undesirably water sensitive dried film; usually 3 to 6 percent by weight amine is preferred. Another formulation is:

| | | |
|---|---|---|
| Modified polymer of Example VIII | 3 | parts |
| Denatured alcohol | 41.8 | parts |
| Aminomethyl propanol | 0.2 | part |
| Water | 56 | parts |

Addition of a minor amount of a highly hydratable water insoluble organic polymer to the above hair set solutions, such as about 1 part of a carboxymethyl cellulose or similar highly carboxylated polymeric material neutralized with additional amine, will form a gel which may, in some cases, be the preferred form for application to the hair. In still another form, about 5 parts of a moderately water soluble propellant such as dimethyl ether or difluoro ethane was added to provide a foaming formulation.

As is well known, hair spray is customarily applied to the hair after it has been styled into a desired configuration. Solutions and gels are usually applied to hair which is subsequently, while still moist, put up in curlers, rollers, pins, clips, ribbons or the like; when dry, the hair is combed out or brushed. A light application of a spray may be applied to the thus styled hair to significantly improve curl retention.

We claim:

1. A method of styling hair comprising combing and styling hair into a desired configuration and applying to the thus configured hair a liquid hair styling composition capable of holding hair in place under humid and windy conditions while imparting a soft hand and sheen to the hair and which is easily removed by shampooing comprising a polymer solvent and in combination therewith a fluoroaliphatic radical containing modified film-forming polymer, said fluoroaliphatic radical being a fluorinated saturated monovalent nonaromatic radical containing from 3 to 20 carbon atoms, in which the carbon atoms of the chain are substituted only by fluorine, chlorine or hydrogen atoms with no more then one hydrogen or chlorine atom for every two carbon atoms, and in which a divalent oxygen or trivalent nitrogen atom, bonded only to carbon atoms, can be present in the aliphatic chain, said polymer being a linear polar polymer having a specific viscosity in one percent solution in methyl ethyl ketone at 25°C. of at least 0.05, having pendant fluoroaliphatic groups contributing 0.5 to 15 percent by weight fluorine to the polymer, said polymer also containing between five and 22 percent by weight pendant carboxyl groups.

2. Styled hair having adsorbed thereon a thin transparent pliable film of a linear polar polymer having a specific viscosity in one percent solution in methyl ethyl ketone at 25°C. of at least 0.05, having pendant fluoroaliphatic groups comprising a fluorinated saturated monovalent non-aromatic radical containing from 3 to 20 carbon atoms, in which the carbon atoms of the chain are substituted only by fluorine, chlorine or hydrogen atoms with no more than one hydrogen or chlorine atom for every two carbon atoms, and in which a divalent oxygen or trivalent nitrogen atom, bonded only to carbon atoms, can be present in the aliphatic chain, said pendant fluoroaliphatic groups contributing 0.5 to 15 percent by weight fluorine to the polymer, said polymer also containing between five and 22 percent by weight pendant carboxyl groups, said filmm imparting to the hair a soft hand and glossy sheen and being capable of holding the styled hair in place under conditions of high humidity and mechanical agitation.

3. A liquid hair styling composition capable of holding hair in place under humid and windy conditions while imparting a soft hand and sheen to the hair and which is easily removed by shampooing comprising a polymer solvent and in combination therewith a fluoroaliphatic radical containing modified film-forming polymer, said fluoroaliphatic radical being a fluorinated saturated monovalent non-aromatic radical containing from 3 to 20 carbon atoms, in which the carbon atoms of the chain are substituted only by fluorine, chlorine or hydrogen atoms with no more than one hydrogen or chlorine atom for every two carbon atoms, and in which a divalent oxygen or trivalent nitrogen atom, bonded only to carbon atoms, can be present in the aliphatic chain, said polymer being a linear polar polymer having a specific viscosity in one percent solution in methyl ethyl ketone at 25°C. of at least 0.05, having pendant fluoroaliphatic groups contributing 0.5 to 15 percent by weight fluorine to the polymer, said polymer also containing between five and 22 percent by weight pendant carboxyl groups.

4. A hair styling composition according to claim 3 wherein the modified film-forming polymer comprises a film-forming copolymer of maleic anhydride and terminally ethylenically unsaturated monomers selected from the group consisting of alkyl vinyl ethers and terminally unsaturated olefins, modified by reaction with a fluoroaliphatic radical containing compound.

5. A hair styling composition according to claim 4 wherein the fluoroaliphatic radical containing compound is represented by the formula $$R_fQ_pZ$$

wherein $R_f$ is a fluorinated saturated monovalent nonaromatic radical containing from 3 to 20 carbon atoms, Q is a divalent linking group, and $p$ is 0 or 1, and Z is a functional radical selected from the group consisting of —OH, —SH and —NRH, where R is H or a lower alkyl group of from one to 4 carbon atoms.

6. A hair styling composition according to claim 3 wherein the modified film-forming polymer comprises a copolymer of maleic anhydride, an alkyl vinyl ether, and a fluoroaliphatic vinyl ether, in molar proportions such that the number of moles of maleic anhydride is substantially equal to the sum of the moles of alkyl vinyl ether and fluoroaliphatic vinyl ether.

7. A modified film-forming polymer suitable for hair styling compositions, said polymer being a linear polar polymer having a specific viscosity in one percent solution in methyl ethyl ketone at 25°C. of at least 0.05, having pendant fluoroaliphatic groups comprising a fluorinated saturated monovalent non-aromatic radical containing from 3 to 20 carbon atoms, in which the carbon atoms of the chain are substituted only by fluorine, chlorine or hydrogen atoms with no more than one hydrogen or chlorine atom for every two carbon atoms, and in which a divalent oxygen or trivalent nitrogen atom, bonded only to carbon atoms, can be present in the aliphatic chain, said pendant fluoroaliphatic groups contributing 0.5 to 15 percent by weight of fluorine to the polymer, said polymer also containing between five and 22 percent by weight pendant carboxyl groups.

* * * * *

UNITED STATES PATENT AND TRADEMARK OFFICE
CERTIFICATE OF CORRECTION

PATENT NO. : 4,015,612

DATED : April 5, 1977

INVENTOR(S) : FRANK J. PAVLIK and ROBERT L. HANSEN

It is certified that error appears in the above-identified patent and that said Letters Patent are hereby corrected as shown below:

Column 6, line 23 change "or" to -- of --.

Column 9, line 51 change "nirogen" to -- nitrogen --.

Column 10, Example V(e), line 29, change "1/2" to -- 1/8 --.

Column 12, line 13 change "filmm" to -- film --.

*Signed and Sealed this*

Twenty-first *Day of* June 1977

[SEAL]

Attest:

RUTH C. MASON
*Attesting Officer*

C. MARSHALL DANN
*Commissioner of Patents and Trademarks*